(12) United States Patent
Denis et al.

(10) Patent No.: US 11,555,303 B2
(45) Date of Patent: Jan. 17, 2023

(54) PLUMBING DRAIN TRAP TREATMENT AND METHOD OF USE

(71) Applicants: Derrick A. Denis, Chandler, AZ (US); Paul V. Anderson, Chandler, AZ (US)

(72) Inventors: Derrick A. Denis, Chandler, AZ (US); Paul V. Anderson, Chandler, AZ (US)

(*) Notice: Subject to any disclaimer, the term of this patent is extended or adjusted under 35 U.S.C. 154(b) by 433 days.

(21) Appl. No.: 16/731,635

(22) Filed: Dec. 31, 2019

(65) Prior Publication Data

US 2020/0208386 A1 Jul. 2, 2020

Related U.S. Application Data

(60) Provisional application No. 62/786,759, filed on Dec. 31, 2018.

(51) Int. Cl.
*E03C 1/28* (2006.01)
*A61L 2/18* (2006.01)

(52) U.S. Cl.
CPC ............... *E03C 1/281* (2013.01); *A61L 2/18* (2013.01)

(58) Field of Classification Search
CPC .................................. E03C 1/281; A61L 2/18
See application file for complete search history.

(56) References Cited

U.S. PATENT DOCUMENTS

| 2011/0162720 A1* | 7/2011 | Ueno | E03C 1/281 137/1 |
| 2016/0151529 A1* | 6/2016 | Rabin | A61L 9/012 512/5 |

* cited by examiner

*Primary Examiner* — Sean E Conley
(74) *Attorney, Agent, or Firm* — Schmeiser Olsen & Watts LP

(57) ABSTRACT

A plumbing drain trap treatment mixture is disclosed. The mixture is poured into a plumbing drain trap to form a layer of the mixture that floats on top of the water in the trap. The mixture layer forms a boundary to prevent evaporation of the water from the trap, thereby maintaining the water in the trap to prevent sewer gas infiltration and pest infiltration to the building. The anti-pest and antimicrobial properties of the mixture may serve to further prevent migration of pests from the sewage drain beyond the trap through the plumbing trap and into the building and/or to protect the barrier itself from microbial infestation. A method of use of a treatment for a plumbing drain trap is also disclosed.

20 Claims, 7 Drawing Sheets

PLUMBING DRAIN TRAP TREATMENT AND METHOD OF USE

CROSS REFERENCE TO RELATED APPLICATION

This application claims priority to U.S. Provisional patent application to Derrick A. Denis and Paul V. Anderson entitled "PLUMBING DRAIN TRAP TREATMENT AND METHOD OF USE," Ser. No. 62/786,759, filed Dec. 31, 2018, the disclosure of which is hereby incorporated entirely herein by reference.

BACKGROUND OF THE INVENTION

Technical Field

This invention relates generally to plumbing drainage systems and more particularly to a treatment for a plumbing drain trap that prevents drying out of the trap.

State of the Art

In conventional plumbing drainage systems under a plumbing fixture with a drain, such as a sink, tub, shower, toilet, floor drain, or the like, sewage wastewater flows through a curved, or "U-shaped," portion of drainage pipe, known as a "trap." In domestic applications, traps are typically U, S, Q, or J-shaped pipe located below or within a plumbing fixture. Wastewater generally flows from the fixture with enough force to go through the trap and out through the drain pipe, leaving a portion of the wastewater to remain in the trap, forming a liquid seal that prevents sewer gas from backing up into the building.

A common problem of plumbing traps is that they can dry out, due to evaporation of the wastewater from the trap, when left unused, underused, or unserviced for extended periods of time, thereby allowing infiltration of sewer gases, as well as sewer pests, into the building.

There are several conventional means of addressing the dry trap issue, each with its respective problems.

For example, one conventional means of addressing the dry trap issue is to actually use the fixture, thereby keeping the trap filled with wastewater. However, this is not always possible or practical, and many fixtures go unused for extended periods of time, allowing the traps to dry out. Another conventional means of addressing the dry trap issue is for employees or vendors to visit such buildings to manually fill each plumbing fixture drain trap with water on a frequently repeating basis, which is a waste of valuable time and money.

Another conventional means of addressing dry traps is to purchase and professionally install mechanical closure devices that allow water to flow into the drain, but close to prevent gases and pests from infiltrating the building. This method is expensive and is merely a work-around. The trap still dries, but the mechanical barrier supplants its purpose. This means requires specifically-sized products, plumbing experts to install and perpetual preventative maintenance to prevent the device from sticking in the open position, thereby allowing sewer gases and pests unhindered access to the site, or sticking in the closed position, resulting in a flooded building because water cannot go down the drain as intended.

Yet another means involves keeping the trap full by the installation of an automated drip or water injection system plumbed into or hovering above the drain. However, this requires the building to be in use to activate the dispensing, requires professional and costly installation and requires perpetual preventative maintenance to prevent the system from becoming stuck in the off (non-emitting) position or in the open position.

Accordingly, what is needed is an improved plumbing drain trap treatment that prevents drying out of the trap and prevents the infiltration of sewer gases and sewer pests.

SUMMARY OF THE INVENTION

The present invention relates generally to plumbing drainage systems and more particularly to a treatment for a plumbing drain trap that prevents drying out of the trap, prevents sewer gases and pests from migrating through the trap, and inhibits microbial growth in the trap.

Disclosed is a treatment for a plumbing trap, the treatment comprising a liquid mixture of white oil and a botanical oil having anti-pest and antimicrobial properties.

In operation, the mixture may be poured into a plumbing drain that has been filled with waste water or other water so as to form a layer of the mixture that floats on top of the water in the trap. The mixture layer forms a boundary to prevent evaporation of the water from the trap, thereby maintaining the water in the trap to prevent sewer gas infiltration to the building. The anti-pest and antimicrobial properties of the mixture serve to protect the mixture from becoming a site for amplification of microbes and other pests. The botanical oil also serves to give the mixture a slight fragrance and helps to allow users to identify various embodiments of the mixture.

A method of use of a treatment for a plumbing trap is also disclosed.

The foregoing and other features and advantages of the present invention will be apparent from the following more detailed description of the particular embodiments of the invention, as illustrated in the accompanying drawings.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF EMBODIMENTS OF THE INVENTION

As discussed above, embodiments of the present invention relate generally to plumbing drainage systems and more particularly to a treatment for a plumbing drain trap that resists drying out of the trap.

As briefly described above, conventional plumbing drainage systems in buildings rely on gravity to pull wastewater along through generally downward-sloping drainage pipes toward a sewage treatment facility or a septic tank. Commonly, under a plumbing fixture with a drain, such as a sink, tub, shower, toilet, or the like, sewage wastewater flows through a curved, or "U-shaped," portion of drainage pipe, known as a "trap." A plumbing drainage trap may also be known, without limitation, as a "P-trap," "S-trap," or "U-trap." Plumbing drainage traps may be of any of a variety of shapes, configured such that a portion of the drain pipe is lower than, or dips below, the level of the surrounding portions of the drain pipe immediately before and after the trap.

Figure 1:
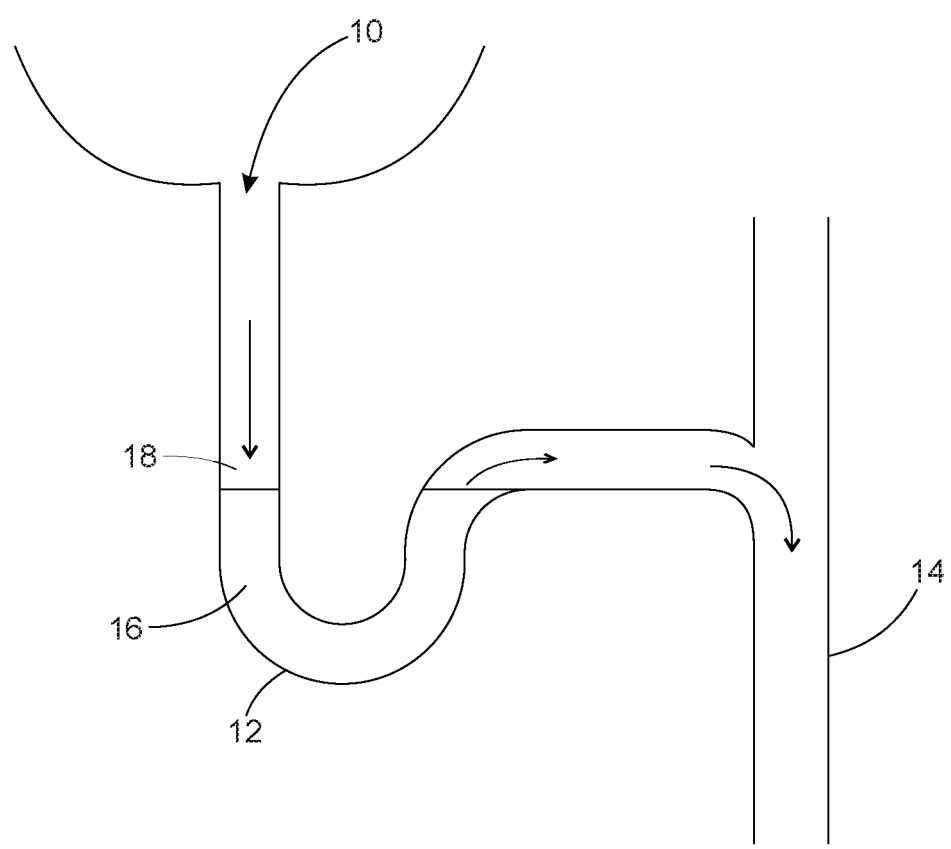
FIG. 1 is a diagrammatic view of a conventional, properly-functioning, plumbing fixture drain trap.

In a properly-functioning conventional drainage system, such as that shown in FIG. 1, wastewater generally flows from the plumbing drain 10 with enough force to go through the trap 12 and out through the drain pipe 14, leaving a portion of the wastewater 16 to remain in the trap 12 afterward, forming a liquid seal that prevents sewer gas and sewer pests (e.g. roaches, sewer flies, etc.) from backing up into the building. As wastewater enters the inlet 18 of the trap 12, an equal amount of wastewater in the trap 12 is thereby forced out of the outlet of the trap 12, leaving a substantially constant amount of wastewater 16 in the trap 12 to maintain the liquid seal. The unnumbered arrows in FIG. 1 indicate the direction of flow of wastewater through the trap.

Figure 2:
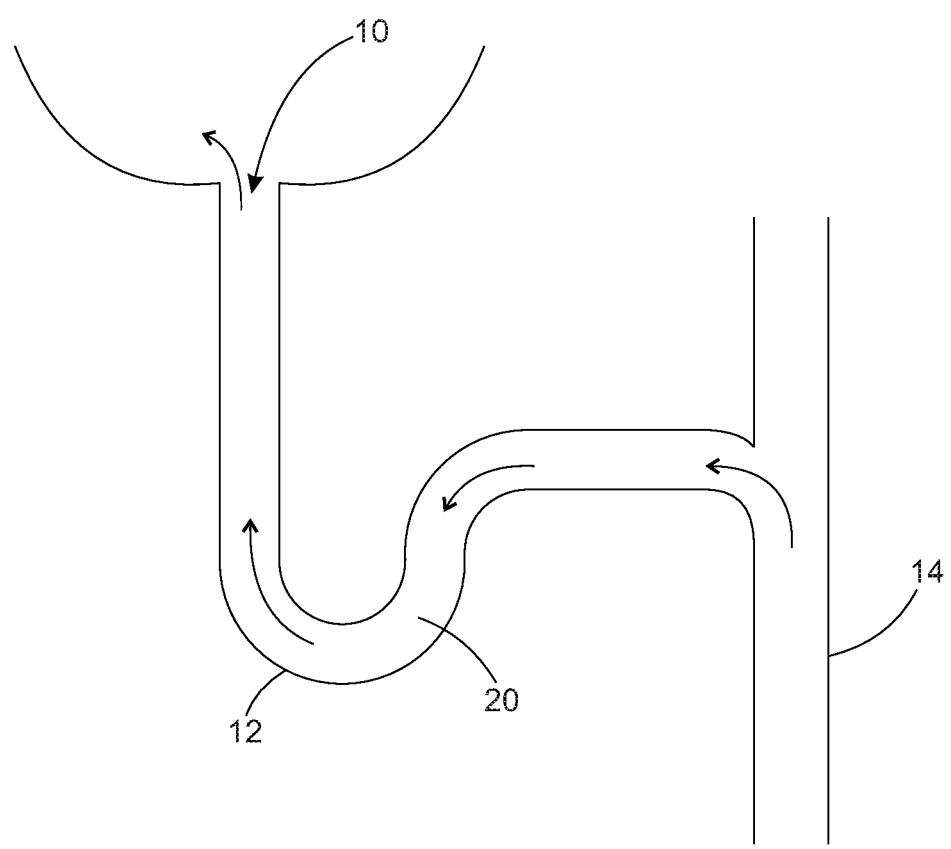
FIG. 2 is a diagrammatic view of a dry conventional plumbing fixture drain trap.

A common problem of plumbing traps is that they can dry out, due to evaporation of the wastewater from the trap, when left unused, underused, or unserviced for extended periods of time. As shown in FIG. 2, a dry trap 12 thereby has an open-air pathway 20, between the sewer system and the building interior, that allows infiltration of sewer gas into the building, as indicated by the arrows in FIG. 2, including, but not limited to, such toxic gases as hydrogen sulfide, ammonia, methane, methyl mercaptan, carbon dioxide, and sulfur-dioxide. The unnumbered arrows in FIG. 2 indicate the direction of flow of sewer gases through the trap. Infiltration of sewer gas into the building is a human health and safety problem. Among other things, it creates an unpleasant nuisance odor; can irritate mucosal membranes; may poison or asphyxiate; and it can damage fire life and safety equipment, such as smoke detectors and fire alarm panels, causing failures to function or inadvertent activations. It may also corrode metals, such as metals used in plumbing fixture finishes, electrical components, and fire alarms, for example. Exposure to sewer gases can result in olfactory fatigue, so building occupants can no longer detect the odor or the intensity of gases but may still be receiving a substantive or ever-increasing dose.

Besides infiltration of sewer gases, dry traps may allow unfettered infiltration of sewer pests to the building, including cockroaches, drain flies, rodents, and the like.

The dry trap issue plagues buildings throughout the world, impacting commercial property managers with unoccupied spaces for lease; residential realtors with vacant listings; building owners with concealed plumbing fixtures, such as mop sinks and floor drains; empty-nesters with unused bathrooms; owners of second homes or vacation homes that remain vacant for extended periods of time; school buildings vacated over summer or winter breaks; vacant hotel rooms; and the like.

A conventional means of addressing the dry trap issue, for such building owners, realtors, property managers, and the like, is to pay employees or vendors to visit such properties to manually fill each plumbing fixture drain trap with water on a frequently repeating basis such as weekly, bi-weekly, or monthly. This conventional means of treating dry traps is a waste of valuable time and money for the stakeholders. Furthermore, when time or budgets run short, this is often among the first preventative maintenance tasks to be omitted.

Another conventional means of addressing dry traps is to buy and professionally install mechanical closure devices that allow water to flow into the drain, but close to prevent gases and pests from infiltrating the building. This method is expensive and is merely a work-around. The trap still dries, but the mechanical barrier supplants its purpose. This means requires specifically sized products, plumbing experts to install and perpetual preventative maintenance to prevent the device from sticking in the open position, thereby allowing sewer gases and pest unhindered access to the site, or sticking in the closed position, resulting in a flooded building because water cannot go down the drain as was its intention.

Yet another means involves keeping the trap full by the installation of an automated drip or water injection system plumbed into or hovering above the drain. However, this requires the building to be in use to activate the dispensing, requires professional and costly installation and requires perpetual preventative maintenance to prevent the system from becoming stuck in the off (non-emitting) position or in the open position.

Dry traps often lead to business interruptions and unnecessary costs due to such conditions as unfavorable customer reviews, employee presenteeism, employee absenteeism, false accusations of mold infestation or natural gas leaks, building evacuations, medical expenses and legal fees. Some of these conditions further result in waste of time and resources of public health and safety officials, first responders, and the like.

Disclosed is a treatment for a plumbing trap, that prevents drying out of the trap, the treatment comprising a liquid mixture of white oil (also known as mineral oil or divider oil) and a botanical oil having anti-pest and antimicrobial properties. In embodiments, the mixture may comprise from 10% to 99.9% by liquid volume white oil and from 0.1% to 90% by liquid volume botanical oil, with a preferred embodiment comprising from 90% to 99.9% by liquid volume white oil and 0.1% to 10% by liquid volume botanical oil. In a preferred embodiment, the white oil is Certified Organic Grade 70. Also, in a preferred embodiment, the botanical oil is peppermint oil. However, in other embodiments, the botanical oil may be any of the group of botanical oils including peppermint oil, spearmint oil, tea tree oil, thyme oil, lemongrass oil, rosemary oil or any combination thereof.

The mixture may be colorless, inert and immiscible with water. It may have a density (specific gravity) range of 0.800 to 0.900 at 25 C, a flash point range of 275 F to 550 F, a pour point (freeze point) range of −40 F to 20 F, viscosity (Saybolt universal viscosity at 100 F) range of 40 to 2100, volatility (evaporation rate/lower boiling point) range of 649 F or greater, and a lower carbon limit of greater than C20.

Figure 3:
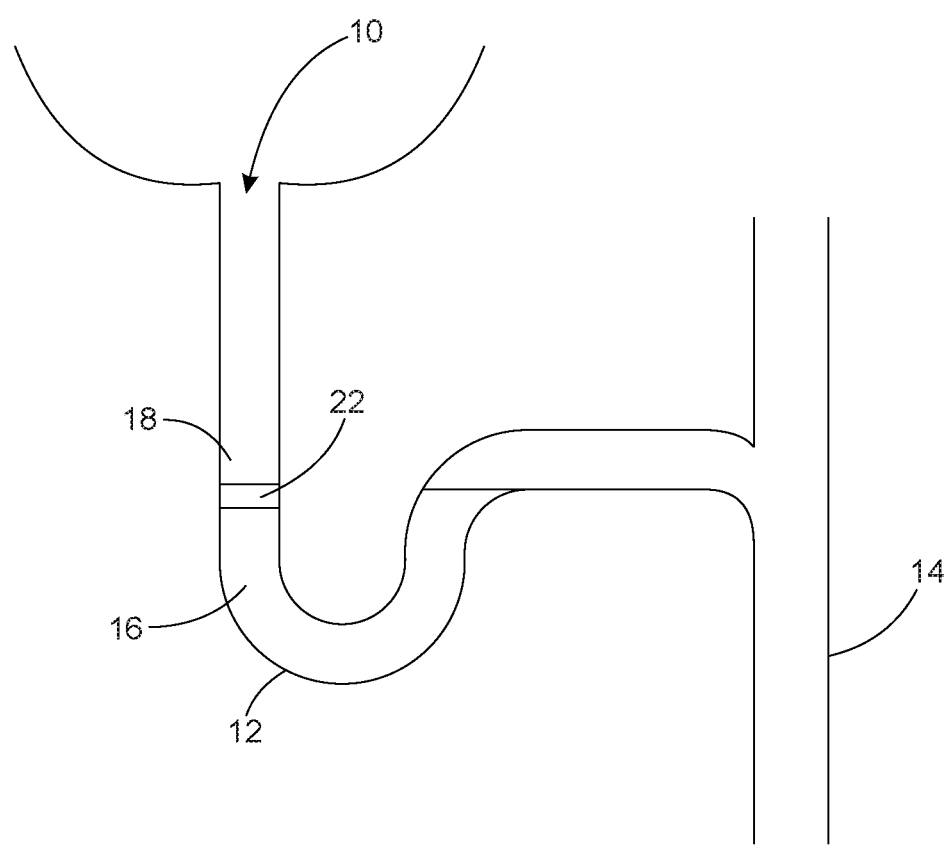
FIG. 3 is a diagrammatic view of a plumbing fixture drain trap with applied treatment mixture, in accordance with an embodiment.

In operation, as shown in FIG. 3, a sufficient amount of the mixture may be poured into a plumbing drain 10 to form a layer of the mixture 22 on top of the water 16 in the trap 12. The mixture 22, having a lower density than the water 16, floats on top of the water 16. The mixture layer 22 forms a boundary to prevent evaporation of the water 16 from the trap 12, thereby maintaining the water 16 in the trap 12 to prevent sewer gas infiltration to the building. The anti-pest and antimicrobial properties of the mixture 22 may serve to prevent migration of pests from the sewage drain beyond the trap 12 through the plumbing drain 10 and into the building and/or to protect the barrier itself from microbial infestation. The botanical oil may also serve to give the mixture a slight fragrance that is pleasant and helps to allow users to identify various embodiments of the mixture. It is contemplated that an embodiment may comprise less than 0.1% by liquid volume botanical oils.

With some use of a plumbing fixture to which the mixture is applied, water may pass through the mixture, allowing the mixture to remain in place, the mixture floating on the water in the trap. With moderate use, a portion of the product may pass through the water and form an evaporation barrier on the sewer side of the trap in addition to the barrier on the building side of the trap. With even more use, the mixture may be ultimately washed through the trap and into the sewer drain pipe, leaving only water in the trap, necessitating additional application of the mixture. However, over prolonged periods of non-use of a fixture to which the mixture has been applied, the mixture will remain in place, thereby preventing evaporation of water in the trap, and maintaining the sewer gas barrier. Under typical conditions of non-use, some embodiments of the mixture may remain in place, with no water evaporation, for periods of up to 2-3 years or longer.

Figure 4:
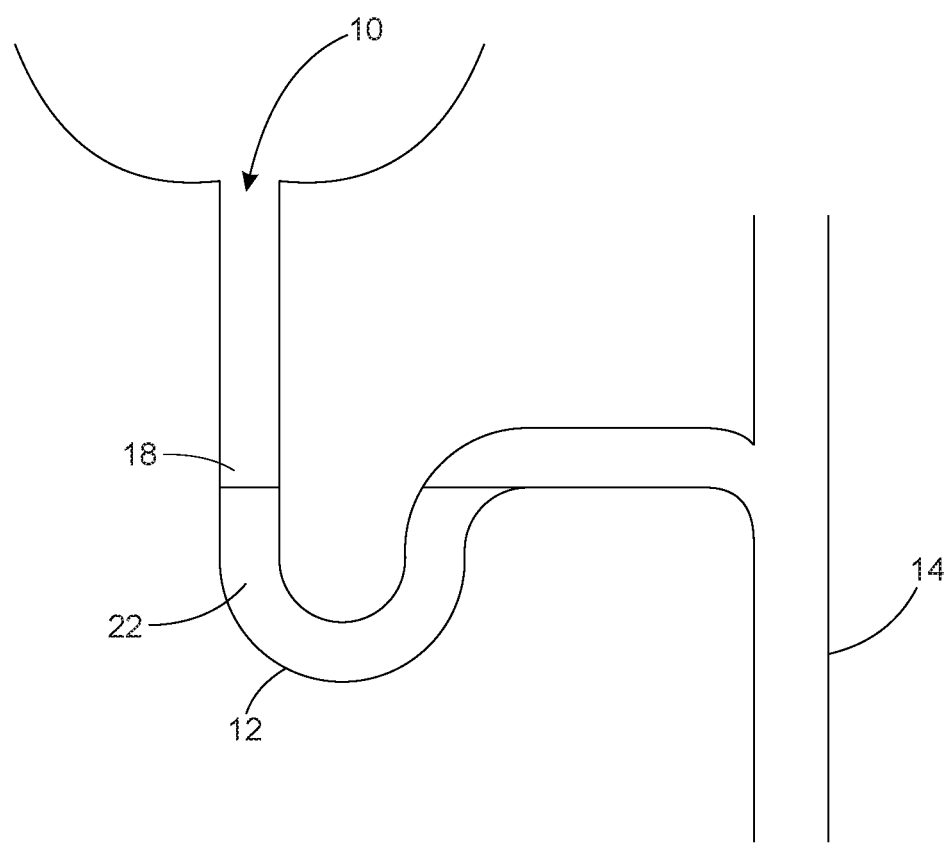
FIG. 4 is a diagrammatic view of a plumbing fixture drain trap with an alternatively applied treatment mixture, in accordance with an embodiment.

In an alternative application, as shown in FIG. 4, a sufficient amount of the mixture may be poured into a plumbing drain 10, with a dry trap having no water, to form a sewer gas infiltration barrier without water.

Figure 5A:
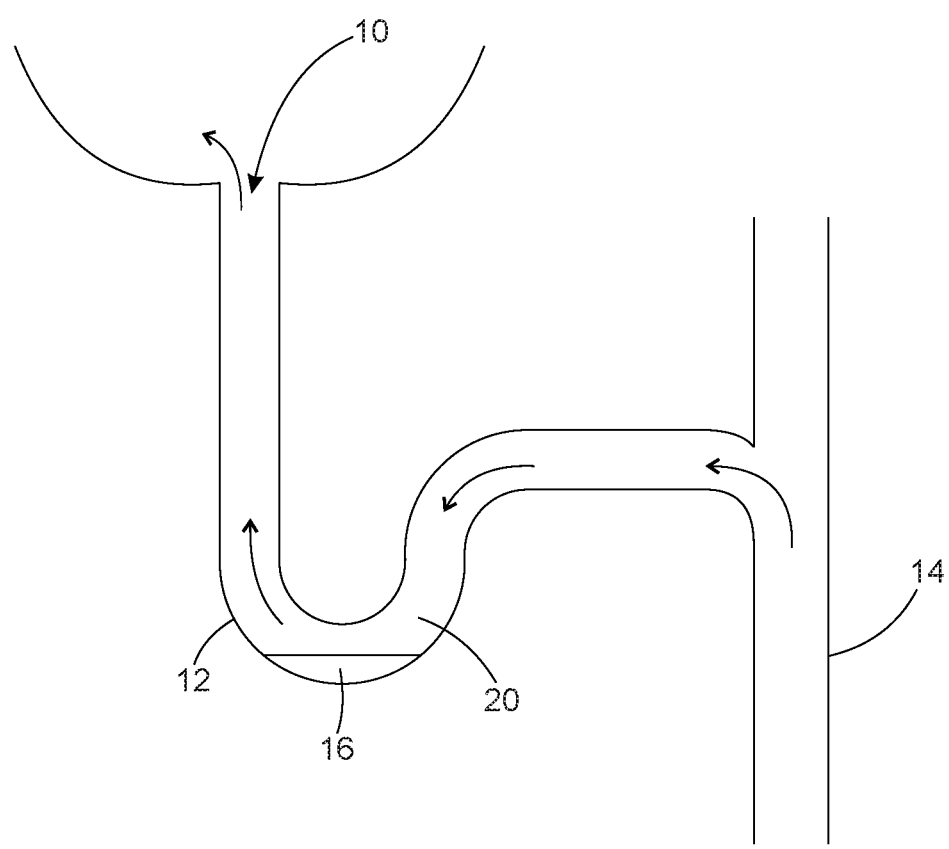
FIG. 5A is a diagrammatic view of a partially-dry conventional plumbing fixture drain trap.
Figure 5B:
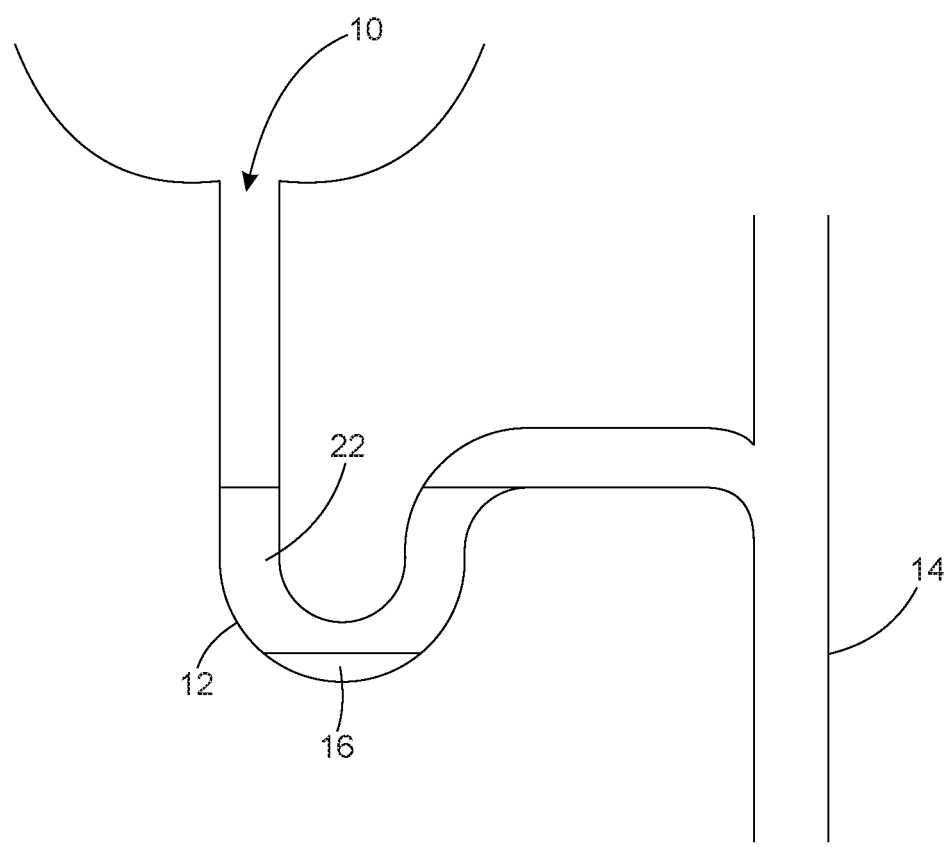
FIG. 5B is a diagrammatic view of a plumbing fixture drain trap with an alternatively-applied treatment mixture, in accordance with an embodiment.

In another alternative application, as shown in FIG. 5A, a partially dry trap 12 may have some water 16 remaining in the bottom of the trap 12. However, there is not enough water 16 to seal the open-air pathway 20. The unnumbered arrows in FIG. 5A indicate the direction of flow of sewer gases through the trap. As shown in FIG. 5B, a sufficient amount of the mixture 22 may be poured into the plumbing drain 10, with a partially dry trap 12, to complete the liquid seal.

Although some embodiments of the present invention discussed herein, including in the drawings, are presented as intended for application to a plumbing drain trap located below a basin, such as a sink or a tub, this is not intended to be limiting. Embodiments of the present invention may be applied to any plumbing drain trap. For example, embodiments of the present invention may be applied to any plumbing drain trap disposed below any plumbing fixture with a drain, such as a sink, tub, shower, floor drain, wash basin, toilet, mop sink, or the like. Embodiments of the present invention may also be applied to any plumbing drain trap in applications that do not include a plumbing fixture, such as a floor drain, for example.

Figure 6:
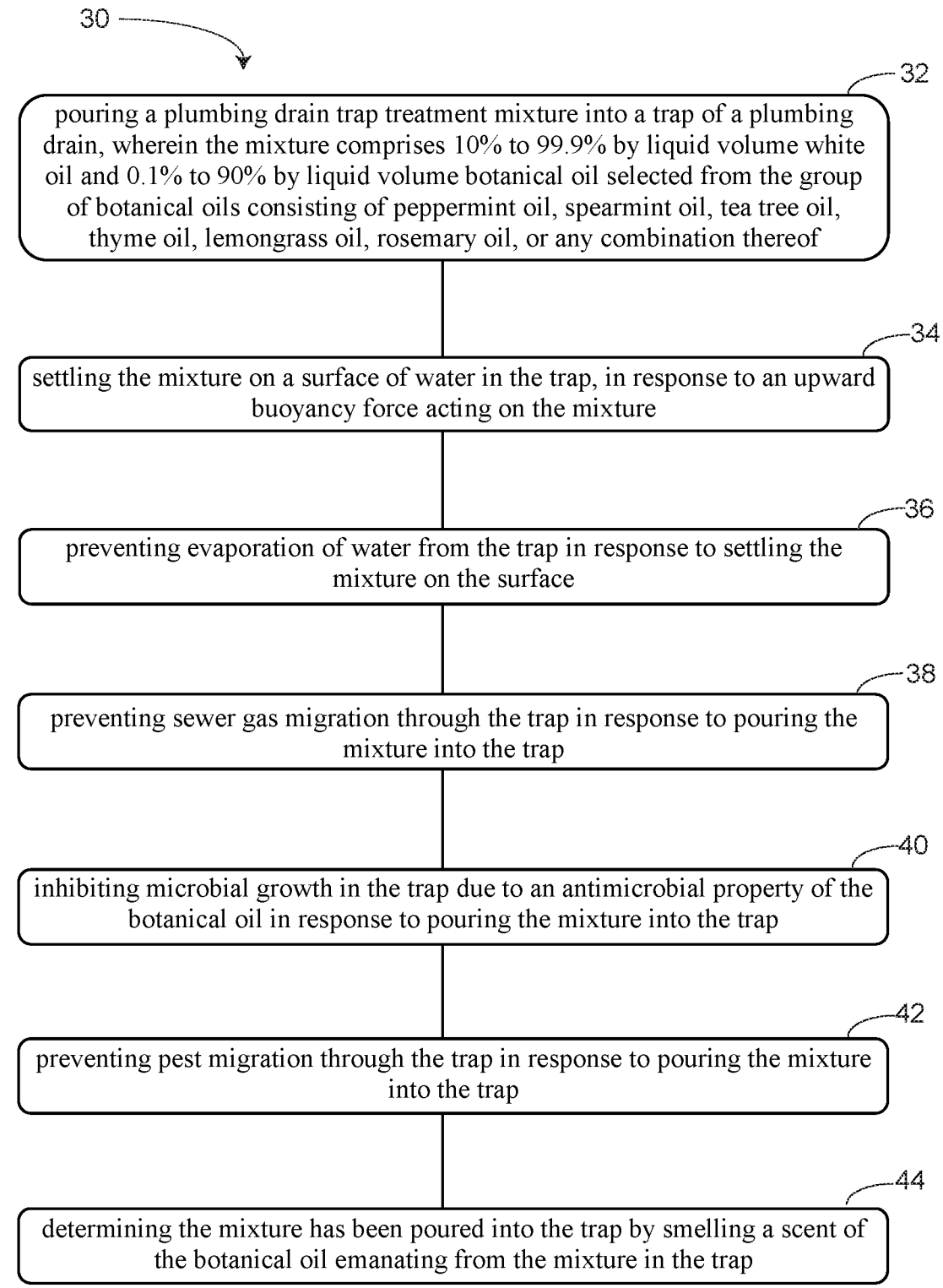
FIG. 6 is a block diagram of a method of using a plumbing drain trap treatment mixture, according to an embodiment.

FIG. 6 is a block diagram showing steps of a method 30 of using a plumbing drain trap treatment mixture, the method comprising the steps: pouring a plumbing drain trap treatment mixture into a trap of a plumbing drain, wherein the mixture comprises 10% to 99.9% by liquid volume white oil and 0.1% to 90% by liquid volume botanical oil selected from the group of botanical oils consisting of peppermint oil, spearmint oil, tea tree oil, thyme oil, lemongrass oil, rosemary oil, or any combination thereof [Step 32]; settling the mixture on a surface of water in the trap, in response to an upward buoyancy force acting on the mixture [Step 34]; preventing evaporation of water from the trap in response to settling the mixture on the surface [Step 36]; preventing sewer gas migration through the trap in response to pouring the mixture into the trap [Step 38]; inhibiting microbial growth in the trap due to an antimicrobial property of the botanical oil in response to pouring the mixture into the trap [Step 40]; preventing pest migration through the trap in response to pouring the mixture into the trap [Step 42]; and determining the mixture has been poured into the trap by smelling a scent of the botanical oil emanating from the mixture in the trap [Step 44].

In some embodiments of a method 30 of using a plumbing trap treatment mixture, the trap may be dry prior to Step 32; Steps 34 and 36 may be omitted; and the method 30 may further comprise the step of forming a liquid seal in the trap in response to pouring the mixture into the drain. In other embodiments of a method 30 of using a plumbing trap treatment mixture, the trap may contain some water, such as is illustrated in FIG. 5A, in an amount that is insufficient to form a water seal, and the method 30 may further comprise the step of forming a liquid seal in the trap in response to pouring the mixture into the drain. In yet other embodiments of a method 30 of using a plumbing trap treatment mixture, the mixture may comprise 90% to 99.9% by liquid volume white oil, wherein the white oil is Certified Organic Grade 70 white oil; and 0.1% to 10% by liquid volume peppermint oil.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

What is claimed is:

1. A method of using a plumbing drain trap treatment mixture, the method comprising:
   pouring the mixture into a trap of a plumbing drain; and
   preventing sewer gas migration through the trap in response to pouring the mixture into the trap, wherein the mixture comprises:
   10% to 99.9% by liquid volume white oil; and
   0.1% to 90% by liquid volume botanical oil selected from the group of botanical oils consisting of peppermint oil, spearmint oil, tea tree oil, thyme oil, lemongrass oil, rosemary oil, or any combination thereof.

2. The method of using a plumbing drain trap treatment mixture of claim 1, wherein, before the mixture is poured into the drain, the trap is dry, the method further comprising:
   forming a liquid seal in the trap in response to pouring the mixture into the drain.

3. The method of using a plumbing drain trap treatment mixture of claim 1, wherein, before the mixture is poured into the drain, the trap contains a water seal, the method further comprising:
   settling the mixture on a surface of the water seal, in response to an upward buoyancy force acting on the mixture; and
   preventing evaporation of water from the trap in response to settling the mixture on the surface.

4. The method of using a plumbing drain trap treatment mixture of claim 1, wherein, before the mixture is poured into the drain, the trap contains some water in an amount insufficient to form a liquid seal in the trap, the method further comprising:

settling the mixture on a surface of the water, in response to an upward buoyancy force acting on the mixture; and
forming a liquid seal in the trap in response to pouring the mixture into the drain.

5. The method of using a plumbing drain trap treatment mixture of claim 4, the method further comprising:
preventing evaporation of water from the trap in response to settling the mixture on the surface.

6. The method of using a plumbing drain trap treatment mixture of claim 1, the method further comprising:
inhibiting microbial growth in the trap and in the mixture due to an antimicrobial property of the botanical oil in response to pouring the mixture into the trap.

7. The method of using a plumbing drain trap treatment mixture of claim 1, the method further comprising:
preventing pest migration through the trap in response to pouring the mixture into the trap.

8. The method of using a plumbing drain trap treatment mixture of claim 1, the method further comprising:
determining the mixture has been poured into the trap by smelling a scent of the botanical oil emanating from the mixture in the trap.

9. A method of using a plumbing drain trap treatment mixture, the method comprising:
pouring the mixture into a trap of a plumbing drain; and
preventing sewer gas migration through the trap in response to pouring the mixture into the trap, wherein the mixture comprises:
90% to 99.9% by liquid volume white oil; and
0.1% to 10% by liquid volume peppermint oil.

10. The method of using a plumbing drain trap treatment mixture of claim 9, wherein, before the mixture is poured into the drain, the trap is dry, the method further comprising:
forming a liquid seal in the trap in response to pouring the mixture into the drain.

11. The method of using a plumbing drain trap treatment mixture of claim 9, wherein, before the mixture is poured into the drain, the trap contains a water seal, the method further comprising:
settling the mixture on a surface of the water seal, in response to an upward buoyancy force acting on the mixture; and
preventing evaporation of water from the trap in response to settling the mixture on the surface.

12. The method of using a plumbing drain trap treatment mixture of claim 9, wherein, before the mixture is poured into the drain, the trap contains some water in an amount insufficient to form a liquid seal in the trap, the method further comprising:
settling the mixture on a surface of the water, in response to an upward buoyancy force acting on the mixture; and
forming a liquid seal in the trap in response to pouring the mixture into the drain.

13. The method of using a plumbing drain trap treatment mixture of claim 12, the method further comprising:
preventing evaporation of water from the trap in response to settling the mixture on the surface.

14. The method of using a plumbing drain trap treatment mixture of claim 9, the method further comprising:
inhibiting microbial growth in the trap and in the mixture due to an antimicrobial property of the peppermint oil in response to pouring the mixture into the trap.

15. The method of using a plumbing drain trap treatment mixture of claim 9, the method further comprising:
preventing pest migration through the trap in response to pouring the mixture into the trap.

16. The method of using a plumbing drain trap treatment mixture of claim 9, the method further comprising:
determining the mixture has been poured into the trap by smelling a scent of the peppermint oil emanating from the mixture in the trap.

17. A method of using a plumbing drain trap treatment mixture, wherein the mixture comprises:
99% to 99.9% by liquid volume white oil, wherein the white oil is Certified Organic Grade 70 white oil; and
0.1% to 1% by liquid volume peppermint oil, the method comprising:
pouring the mixture into a trap of a plumbing drain;
preventing sewer gas migration through the trap in response to pouring the mixture into the trap;
inhibiting microbial growth in the trap and in the mixture due to an antimicrobial property of the peppermint oil in response to pouring the mixture into the trap;
preventing pest migration through the trap in response to pouring the mixture into the trap; and
determining the mixture has been poured into the trap by smelling a scent of the peppermint oil emanating from the mixture in the trap.

18. The method of using a plumbing drain trap treatment mixture of claim 17, wherein, before the mixture is poured into the drain, the trap is dry, the method further comprising:
forming a liquid seal in the trap in response to pouring the mixture into the drain.

19. The method of using a plumbing drain trap treatment mixture of claim 17, wherein, before the mixture is poured into the drain, the trap contains a water seal, the method further comprising:
settling the mixture on a surface of the water seal, in response to an upward buoyancy force acting on the mixture; and
preventing evaporation of water from the trap in response to settling the mixture on the surface.

20. The method of using a plumbing drain trap treatment mixture of claim 17, wherein, before the mixture is poured into the drain, the trap contains some water in an amount insufficient to form a liquid seal in the trap, the method further comprising:
settling the mixture on a surface of the water, in response to an upward buoyancy force acting on the mixture;
forming a liquid seal in the trap in response to pouring the mixture into the drain; and
preventing evaporation of water from the trap in response to settling the mixture on the surface.

* * * * *